United States Patent [19]

Parrillo et al.

[11] 4,351,343
[45] Sep. 28, 1982

[54] ECG PATIENT MONITORING LEAD ASSEMBLY

[75] Inventors: Michael R. Parrillo, Endwell, N.Y.; John C. Colwell, Hoffman Estates, Ill.

[73] Assignee: Bunker Ramo Corporation, Oak Brook, Ill.

[21] Appl. No.: 183,137

[22] Filed: Sep. 2, 1980

[51] Int. Cl.³ .............................................. A61B 5/00
[52] U.S. Cl. ................................................. 128/695
[58] Field of Search ....................... 128/695, 696, 639;
174/65 G; 339/61 C, 61 M, 103 B

[56] References Cited

U.S. PATENT DOCUMENTS

| 3,323,514 | 6/1967 | Barrett, Jr. | 128/696 |
| 3,510,628 | 5/1970 | Zahaykevich | 174/65 G |
| 4,215,236 | 7/1980 | Reiser | 128/696 |

*Primary Examiner*—William E. Kamm
*Attorney, Agent, or Firm*—Nicholas A. Camasto

[57] ABSTRACT

A multi-contact, feed through connector within a junction box connects patient monitoring electrode leads to a bulk cable which is coupled to ECG apparatus. Access to the interior of the junction box is provided for purposes of replacing the electrode leads when and if needed. Strain relief means are provided for isolating the connector from forces transmitted by the patient monitoring leads.

18 Claims, 3 Drawing Figures

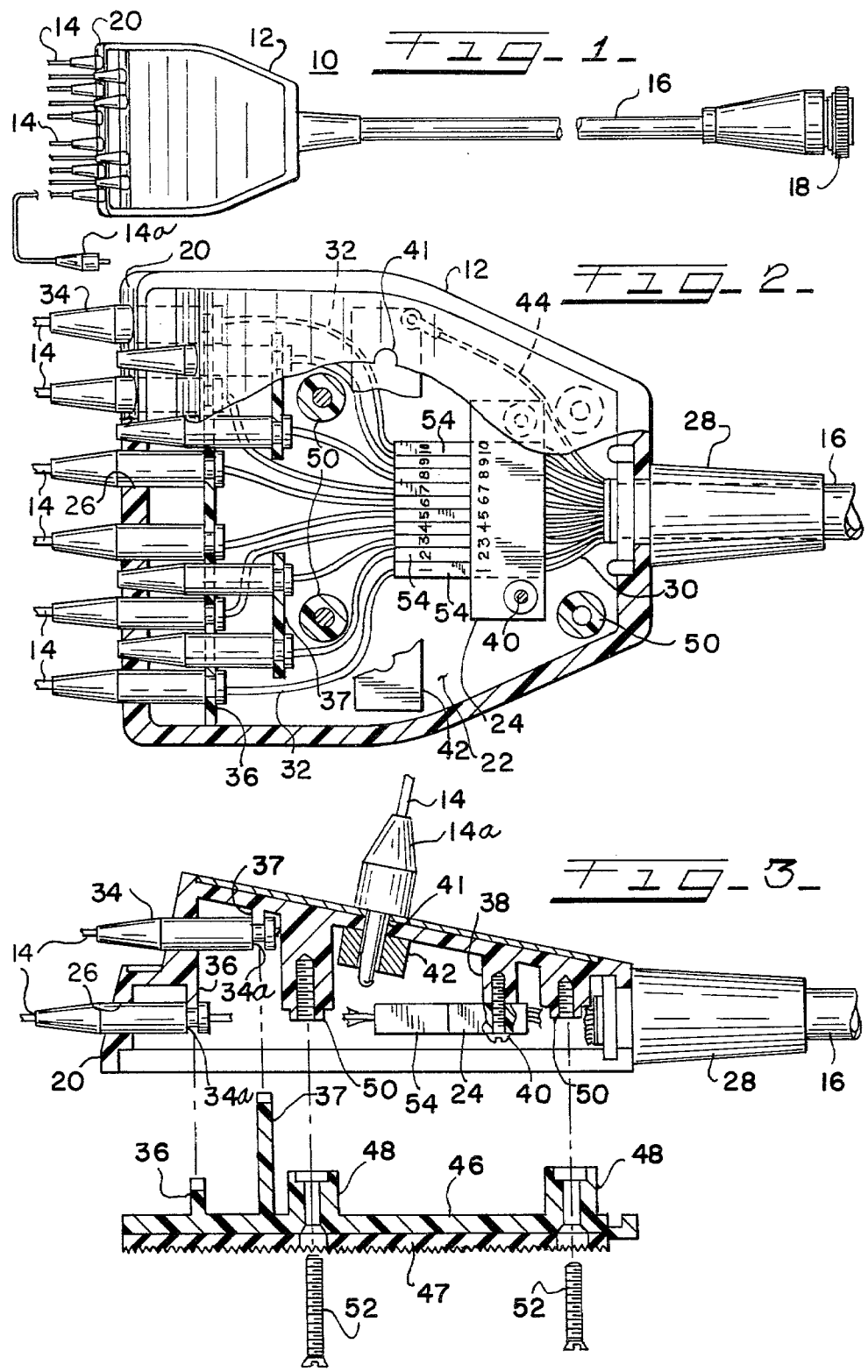

ECG PATIENT MONITORING LEAD ASSEMBLY

FIELD OF THE INVENTION

This invention relates to ECG patient monitoring lead assemblies having provision for removably connecting a plurality of patient monitoring leads to a bulk cable coupled to ECG apparatus.

BACKGROUND OF THE INVENTION AND PRIOR ART

In the field of medical technology, considerable use has been made of electrical monitoring equipment such as electrocardiograph (ECG) apparatus. In using ECG equipment it is common practice to attach a plurality of body electrodes to a patient which are engageable by shielded-conductor patient monitoring leads having suitable electrode attachment terminal clips or plugs. The several monitoring leads are connected, through a junction box, to corresponding conductors in a so-called bulk cable, the latter comprising a plurality of shielded-conductor ECG leads, all surrounded by an additional foil-type shield, and being connected back to the ECG equipment. The patient monitoring leads extending from the junction box are subjected to considerable wear, often to the extent of requiring replacement. Depending upon use, a monitoring lead may need replacement every two or three months.

Prior art patient monitoring lead assemblies include junction boxes generally having a plurality of surface-mounted jacks. The leads are individually plugged into these jacks and are readily replaceable in the event of failure or breakage. Many types of jacks are used including phone jacks, coaxial jacks and arrangements in which the mating plug and jack are threaded or otherwise "locked" together. Naturally, the large number of individual jacks and their mounting arrangements tends to complicate the box design.

The individual jacks have generally high reliability, since they are designed for a great number of mating-unmating operations. Such jacks are underutilized in an ECG environment because of the relatively few mating-unmating operations and are not cost-effective. Further, with the exception of the very expensive locked arrangements, it is difficult to provide strain relief for the monitoring leads without increasing the wear-and-tear on the jack and plug assembly. It is thus not unusual to experience high failure rates in the plug and jack assemblies despite the fact that they are designed for more mating-unmating cycles than are encountered in normal ECG use. This has been a continuing problem in the ECG field.

When the nature of the ECG cable assembly and its use is considered the apparent inconsistency between poor field reliability experience and the use of relatively high reliability components may be reconciled. In an ECG environment the patient monitoring leads coming from the junction box are by-and-large unsupported. The leads extend in different directions and tend to tangle quite easily, which subjects them to bending moments and consequent strain on the connections at the junction box. Therefore, it is believed that the prior art use of jack and plug connections in these junction boxes has not been conducive to high reliability.

The present invention is based upon the operational environment of the ECG junction box and departs from the prior art in that it involves removing the connections to a protected area within the junction box itself, incorporating a low cost semi-permanent type of connector device and providing adequate strain relief of the individual monitoring leads away from the connection points. This is achieved with the system of the invention while retaining the desirable features of the prior art. Though the procedure for field replacement of defective patient monitoring leads is more complex (in the preferred embodiment an openable portion or access panel is removable to allow access to the interior of the junction box), the resultant saving in wear-and-tear on patient monitoring leads and connection points and the improved reliability is more than sufficient compensation.

SUMMARY OF THE INVENTION

A primary object of the present invention is to provide an improved ECG patient monitoring lead assembly.

Another object of the invention is to provide an economical ECG patient monitoring lead assembly of improved reliability.

In accordance with the invention, an ECG patient monitoring lead assembly comprises a number of replaceable patient monitoring leads, a junction box including internal connection means for interconnecting corresponding ones of the monitoring leads and ECG leads and strain relief means for isolating the connection means from forces transmitted by the monitoring leads.

BRIEF DESCRIPTION OF THE DRAWINGS

These and other objects and advantages of the invention will become apparent from the following description taken together with the accompanying drawings wherein like reference characters denote like parts.

FIG. 1 is a partial view of an ECG patient monitoring lead assembly in accordance with the invention.

FIG. 2 is an enlarged partially cut away view of the junction box of FIG. 1.

FIG. 3 is a side elevational sectional view of the junction box of FIG. 2 with the openable portion removed.

DETAILED DESCRIPTION OF THE PREFERRED EMBODIMENT

In FIG. 1 an ECG patient monitoring lead assembly 10 includes a junction box 12, a plurality of patient monitoring leads 14 and a bulk cable 16 comprising a plurality of ECG leads corresponding in number to the patient monitoring leads. The monitoring and ECG leads each include center conductors and surrounding shields. The bulk cable further includes an additional metal foil shield surrounding the ECG leads. The monitoring leads individually enter a left wall 20 of the junction box and are connected to corrresponding ECG leads inside the box. The other ends (only one of which is shown in this FIGURE) of the monitoring leads terminate in plugs 14a adapted for connection to body electrodes on a patient in a well known manner. The bulk cable terminates in a connector 18 for connection of the bulk cable to ECG equipment (not shown).

Referring to FIGS. 2 and 3 junction box 12 defines an internal cavity 22 having a conventional multi-contact connector 24 mounted therein. The box may be made of plastic, for example, and defines a plurality of apertures 26 in wall 20 for supporting elastomeric strain relief grommets 34 individually molded to patient monitoring leads 14. Bulk cable 16 enters the opposite wall of the junction box which includes a clamp arrangement 28 for securing the bulk cable in position. The bulk cable comprises a plurality of ECG leads 30 connected to corresponding sets of contacts of connector 24. Each of ECG leads 30 includes a center conductor and surrounding shield which are crimped, soldered or otherwise electrically connected to appropriate ones of the contacts (not shown) of connector 24. Patient monitoring leads 14, include end portions 32 (understood to represent both center conductors and shields) which are removably connected to connector 24 via a number of dual contact plugs 54. Each lead 14 is secured to box 12 in its associated aperture 26 by elastomeric grommets 34 previously mentioned. These grommets are secured in apertures 26 in an interference fit and provide strain relief for end portions 32 with respect to connector 24. Further strain relief is provided by retention means comprising a retention groove 34a on each grommet adapted for nesting in support baffles 36 or 37.

Connector 24 is mounted to the upper inner surface of box 12 by means of downwardly extending supports 38. Supports 38 are aligned with mounting holes in the ends of the connector and screws 40 hold the connector in position.

A ground strap 42 extends across a portion of the top inner surface of box 12. Should less than all monitoring leads be needed, for example, when treating an amputee, the unused lead should be plugged, via plug 14a, into an opening 41 to electrically connect the center conductor of the lead to the ground strap. Not only is the unused lead kept out of the way, but electrical noise pickup by the unconnected lead is precluded, since the ground bar is connected to grounding conductor 44. Grounding conductor 44 in turn, connects to the bulk cable metal foil shield surrounding the ECG leads which is returned to an electrical ground in the ECG equipment. Although only one unused plug 14a is shown in the top of box 12, it is understood that provision for a number of unused leads is readily made by adding corresponding apertures 41 in the top surface of the box and ground strap 42.

As illustrated in FIG. 3, junction box 12 includes an openable aperture or access panel 46 which also may be made of plastic. Panel 46 provides access to the interior of the junction box for replacement of parts including the patient monitoring leads, the connector and the bulk cable. It will be seen that all of these components may be replaced in the field.

A serrated rubber base 47 is fixed to the bottom of access panel 46 for cushioning and helping the junction box to resist movement when it is placed on a horizontal surface. Panel 46 further includes the lower portion of each support baffle 36 and 37 which, when engaged with the corresponding upper portions of the baffles, engage the annular retention groove 34a in the respective strain relief grommet 34 to positively secure the grommet to the junction box. It should be recognized that the grommets (and corresponding patient monitoring leads) are captivated to the junction box due to the conjoint action of apertures 26, retention grooves 34a, the upper portions of support baffles 36 or 37 and the elastomeric nature of the grommets.

Access panel 46 also includes upwardly extending mounting lugs 48 which mate with mounting lugs 50 extending downwardly from the upper inner surface of the junction box. A threaded fastener 52 is received in each pair of mated mounting lugs 48 and 50 to removably retain the panel.

Connector 24 is a multi-conductor feed-through type connector having ten pairs of vertically-aligned contacts adapted for connection to the individual two-contact plugs 54. End portions 32 of the monitoring leads (and their respective individual shields) are connected to these plugs. The vertically-aligned connector contacts are soldered, crimped or otherwise electrically connected to the corresponding center conductors and shields of ECG leads 30. Connector 24 and the ECG bulk cable are replaceable as a unit should the need arise. The patient monitoring leads with their integral grommets are also readily replaceable by withdrawal of the appropriate one of plugs 54 from connector 24 and removal of its grommet 34 from the junction box.

To facilitate correct connection of the monitoring leads, plugs 54 are numbered to correspond with appropriately numbered contact pairs on connector 24. In the drawings, the indices used are the numbers 1–10.

In practice, replacement of a monitoring lead is accomplished by removing bolts 52 to release access panel 46 and the lower portions of support baffles 36 and 37. The appropriate one of grommets 34 is released from the upper portion of the support baffle, and the corresponding plug 54 disconnected from connector 24 whereupon the monitoring lead, with grommet and plug attached, is removed from the box through aperture 26. In reverse manner, a new monitoring lead may be installed in the box.

Replacement of the ECG bulk cable may be accomplished after removal of the access panel by disengaging connector 18 and clamp arrangement 28 from the ECG apparatus and junction box respectively, and removing screws 40 and connector 24 from the junction box. Necessarily all monitoring lead plugs 54 would be disconnected from connector 24. The ECG bulk cable and connector 24 are re-installed by a reverse procedure.

It will be readily apparent that the ECG patient monitoring lead assembly of the invention isolates the connection points between plugs 54 and connector 24 from forces transmitted by the monitoring leads via grommets 34. Thus a relatively low cost standard multi-contact connector may be used. Not only does a monitoring lead assembly of higher reliability result, but the elimination of the plurality of individual jacks permits a great deal of design freedom.

What is claimed is:

1. An ECG patient monitoring lead assembly comprising:
   a plurality of individually replaceable patient monitoring leads;
   a junction box for receiving a plurality of ECG leads and said plurality of patient monitoring leads;
   connection means in said junction box for electrically inter-connecting corresponding ones of said monitoring leads and said ECG leads; and
   strain relief means independent of said connection means for isolating said connection means from forces transmitted by said patient monitoring leads.

2. The assembly of claim 1, wherein said strain relief means include said junction box; and
   elastomeric means captivating said monitoring leads to said junction box.

3. The assembly as set forth in claim 2 wherein said connection means include;
   a multi-contact connector affixed to said junction box and coupled to said ECG leads; and
   a plurality of removable connectors cooperating with portions of said multi-contact connector for selectively interconnecting said ECG leads and said monitoring leads.

4. The assembly as set forth in claim 3 wherein said multi-contact connector is removably mounted to said junction box, and wherein said plurality of ECG leads are grouped into a bulk cable, and further including;
   means for releasably connecting said bulk cable to said ECG apparatus; and
   means for removably attaching said bulk cable to said junction box to permit field-replacement of said bulk cable.

5. The assembly as set forth in claim 4 wherein said junction box is totally enclosed and includes an openable portion permitting access to the interior.

6. The assembly as set forth in claim 5 wherein said openable portion includes baffle means cooperating with said junction box and said elastomeric means.

7. The assembly as set forth in claim 6 wherein both said multi-contact connector and said plurality of removable connectors are identity-coded to enable proper interconnection thereof.

8. The assembly as set forth in claim 6 therein said monitoring leads are shielded, and further including;
   ground means on said junction box for retention of any unused monitoring leads.

9. The assembly as set forth in claim 2 wherein said elastomeric means comprise elongated strain relief grommets, molded to said monitoring leads, and having retention means formed therein;
   said junction box defining apertures permitting an interference fit with said grommets and including support means cooperating with said retention means for holding said grommets securely in position.

10. The assembly as set forth in claim 9 wherein said junction box is totally enclosed, wherein said support means defines a first support baffle, and further includes;
   an openable portion permitting access to the interior, said openable portion including a second support baffle cooperating with said first support baffle and with said retention means on said grommet.

11. The assembly as set forth in claim 10 wherein said openable portion is affixed by removable fasteners.

12. An ECG patient monitoring lead assembly comprising:
   a plurality of individually replaceable patient monitoring leads;
   a junction box for receiving a plurality of ECG leads and said plurality of patient monitoring leads;
   a multi-contact connector affixed to said junction box and coupled to said ECG leads;
   a plurality of removable connectors cooperable with portions of said multi-contact connector for selectively interconnecting said ECG leads and said patient monitoring leads; and
   strain relief means comprising elastomeric grommets embracing said monitoring leads and cooperating with said junction box for isolating said connector from forces transmitted by said monitoring leads.

13. The assembly of claim 12 wherein said junction box is totally enclosed and includes an access panel permitting access to the interior thereof.

14. The assembly of claim 13 wherein said grommets include retention grooves cooprating with said junction box and said access panel.

15. The assembly of claim 14 wherein both said multi-contact connector and said plurality of removable connectors are identity-coded to facilitate proper interconnection thereof.

16. An ECG patient monitoring lead assembly comprising:
   a junction box;
   a plurality of individually replaceable patient monitoring leads;
   a replaceable bulk cable, including a plurality of ECG leads, having one end terminating in a removable connector for attachment to ECG apparatus;
   a multi-contact connector mounted in said junction box;
   a plurality of individual connectors removably connecting said monitoring leads to said multi-contact connector;
   means connecting individual ones of said ECG leads in said bulk cable to said multi-contact connector;
   a plurality of elastomeric grommets molded about individual ones of said monitoring leads;
   a plurality of openings defined by said junction box and sized such that said elastomeric grommets are an interference fit therein;
   said junction box including support means for cooperation with grooves in said grommets such that said grommets are retained in said junction box when installed; and
   a removable access panel affixed to said junction box and including baffle means for cooperating with the grooves in said grommets and the support means in said junction box for precluding access to said junction box and for enhancing the strain relief provided by said grommets.

17. The assembly of claim 16 wherein said ECG leads and said patient monitoring leads are shielded conductors, and further including;
   ground strap means in said junction box for holding unused patient monitoring leads with the shielded conductors grounded.

18. The assembly of claim 17 wherein both said multi-contact connector and said plurality of removable connectors are identity-coded to facilitate proper interconnection thereof.

* * * * *